United States Patent [19]

Wagner et al.

[11] Patent Number: 5,387,102
[45] Date of Patent: Feb. 7, 1995

[54] LOCKING SCREW

[75] Inventors: Reiner Wagner; Otto Lehnert, both of Ispringen, Germany

[73] Assignee: OBE-Werk Ohnmacht & Baumgartner GmbH & Co. KG, Ispringen, Germany

[21] Appl. No.: 999,576

[22] Filed: Dec. 30, 1992

Related U.S. Application Data

[63] Continuation-in-part of Ser. No. 843,521, Feb. 28, 1992, abandoned.

[30] Foreign Application Priority Data

Nov. 9, 1991 [DE] Germany .................. 9114045[U]

[51] Int. Cl.$^6$ .................. A61C 8/00; F16B 39/34; G02C 5/00
[52] U.S. Cl. .................. 433/173; 411/304; 351/141
[58] Field of Search .............. 433/173, 174, 175, 176, 433/181; 411/109, 168, 302, 303, 304, 369; 351/141, 153

[56] References Cited

FOREIGN PATENT DOCUMENTS 1196397 7/1965 Germany .................. 351/153
2819744 11/1978 Germany .................. 351/153

Primary Examiner—Cary E. O'Connor
Attorney, Agent, or Firm—Dvorak and Traub

[57] ABSTRACT

A locking screw for connecting first and second closing lugs. The first closing lug has an unthreaded through bore and the second closing lug has a tapped bore open to the unthreaded bore. The locking screw has a head to bear on the first closing lug, a screw-threaded shank, to be screwed into the tapped bore, and a neck disposed between and recessed from the head and the shank. The neck is surrounded by a plastic ring, which protrudes from the shank and frictionally engages the unthreaded through bore. The shank has an unthreaded portion adjoining the plastic ring.

20 Claims, 5 Drawing Sheets

FIG. 9A
FIG. 9B
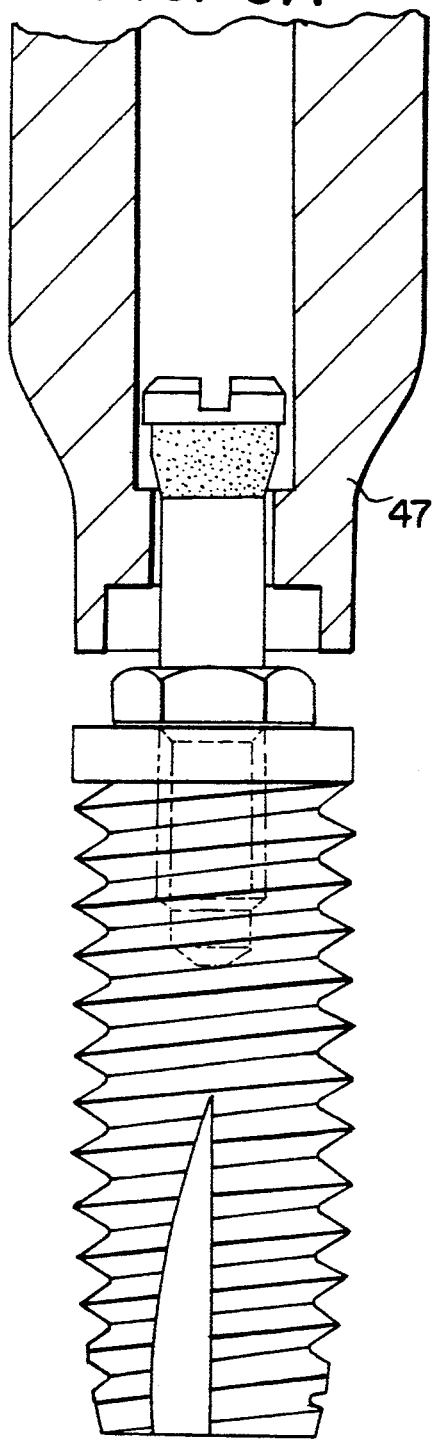
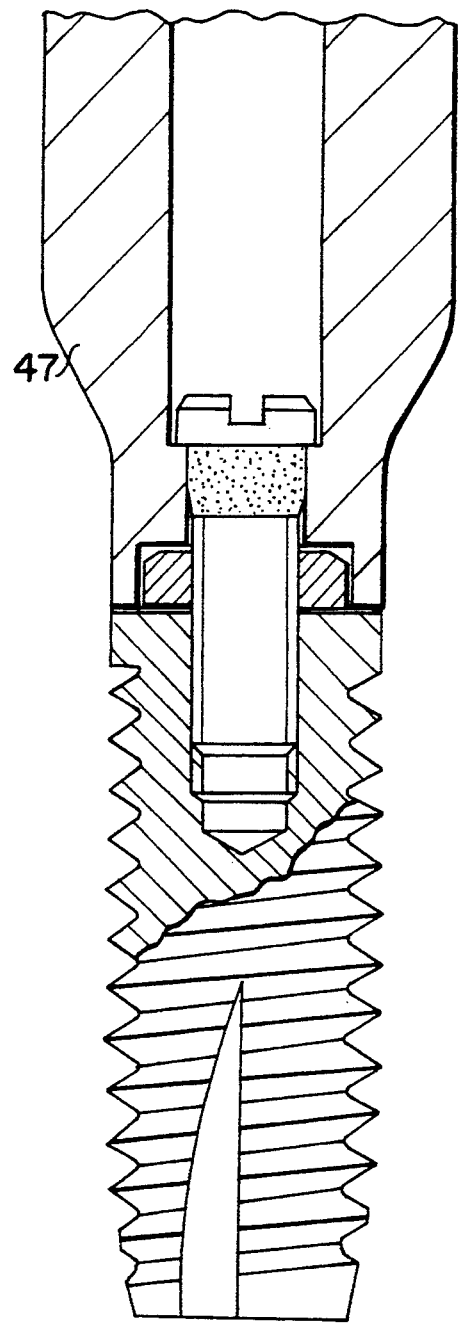

LOCKING SCREW

This application is a continuation-in-part of application Ser. No. 07/843,521, filed Feb. 28, 1992, now abandoned.

BACKGROUND OF THE INVENTION

The present invention relates to a locking screw.

Closing screws for connecting closing lugs generally comprise a head, which bears on or is countersunk in a first closing lug, a neck, which extends through the first closing lug, and a screw-threaded shank, which is screwed in the second closing lug. It has been suggested to provide plastic extrusions in longitudinal grooves formed adjacent to the screw threads of the shank of the locking screw so that the plastic extrusions cooperate with the female screw threads in the second closing lug to lock the screw. After some joining and separating operations, however, the screw threads often destroy the plastic extrusions. In the manufacture of eyeglass frames, for example, and more specifically during the mounting of the lens in the frame, it is necessary to separate and join the closing lugs of the metal rims several times. This action will soon result in destruction of the plastic extrusions which have been inserted into longitudinal grooves of the screw-threaded shanks of the locking screws.

Published German Application 33 35 046 discloses locking screws in combination with small plastic cleats, which are inserted into and anchored in the female screw threads of a second closing lug so that the plastic cleats cooperate with the male screw threads of the shank of the locking screw to lock the latter. The resulting joint, however, will often suffer from the disadvantages outlined above. German Utility Model 88 15 277 discloses a locking screw which is provided under its head with a plastic ring, which cooperates with an annular series of teeth formed in the recess in which the head of the locking screw is received in the first closing lug. The plastic ring will also be destroyed or worn out after several separating operations.

It is, therefore, an object of the present invention to provide a novel locking screw which ensures that there will be virtually no wear at the joint between the closing lugs even after the joint has been separated and restored several times.

The object is accomplished in accordance with the invention by a locking screw having a neck, which is recessed from the shank and surrounded by a plastic ring. The ring may be injection-molded in situ and protrudes from the shank and adjoins an unthreaded portion of the shank. The plastic ring is arranged to frictionally engage an unthreaded through bore of the first closing lug as the locking screw is screwed into the female screw threads of the second closing lug.

BRIEF DESCRIPTION OF THE DRAWINGS

Preferred embodiments of the present invention will now be described more in detail with reference to the following drawings.

FIGS. 9a and 9b are partial sectional views illustrating a locking screw for connecting an implant portion with an abutment.

DETAILED DESCRIPTION OF THE INVENTION

Figure 1:
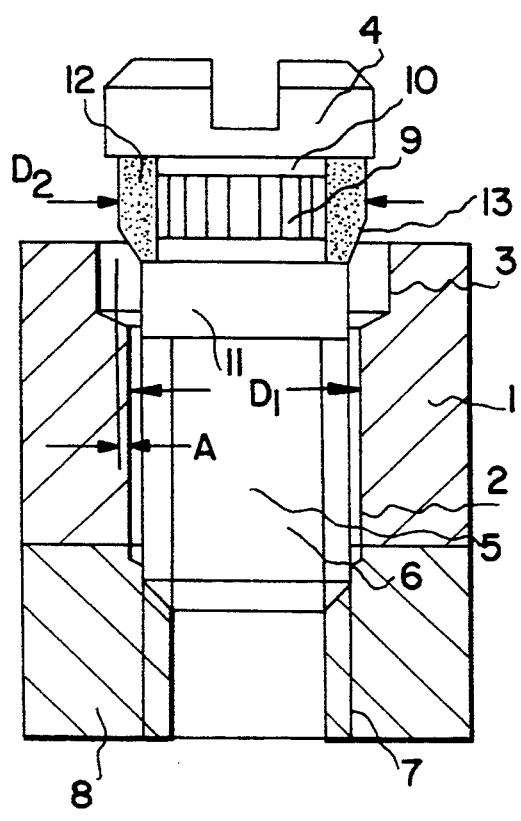
FIG. 1 is a side view of a first embodiment of the present invention.
Figure 2:
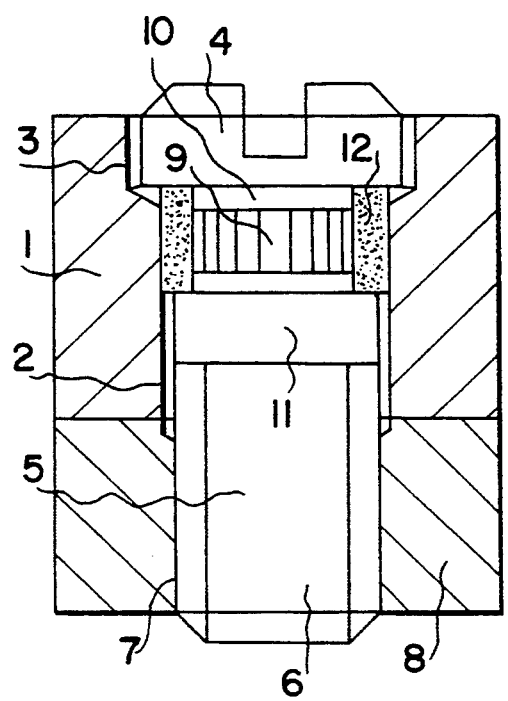
FIG. 2 is also a side view of a first embodiment of the present invention.

In the embodiment shown in FIGS. 1 and 2, the locking screw 5 is used to connect two closing lugs 1 and 8. The lugs 1 and 8 may, for example, be of a metal rim of an eyeglass frame. The first closing lug 1 is formed with an unthreaded through bore and at the top of the bore 2 with a recess 3 for receiving the head 4 of the locking screw 5, which has a shank having a screw-threaded end portion 6 that is screwed into a tapped bore 7 of the second closing lug 8 so that the two closing lugs 1 and 8 are connected.

In that embodiment an unintended separation of the joint is prevented in that the neck of the screw 5 defines an annular recess 10, which is knurled at 9 and is adjoined by an unthreaded top portion 11 of the shank, and the neck is surrounded by a plastic ring 12, which is arranged in the recess 10 and may be injection-molded in place. The plastic ring 12 has a downwardly tapering lower end portion 13. The ratio of the outside diameter $D_2$ of the plastic ring 12 to the diameter $D_1$ of the through bore 2 is preferably 1.05 to 1.09 so that there is an interference A between the plastic ring 12 and the bore 2. The plastic of the ring 12 preferably consists of an amorphous polyether imide. Owing to that design of the locking screw 12 there will be virtually no wear of the plastic ring 12 when the joint between the closing lugs 1 and 8 is separated and restored several times during the manufacture of the eyeglass frame and the mounting of the lens.

Figure 3:
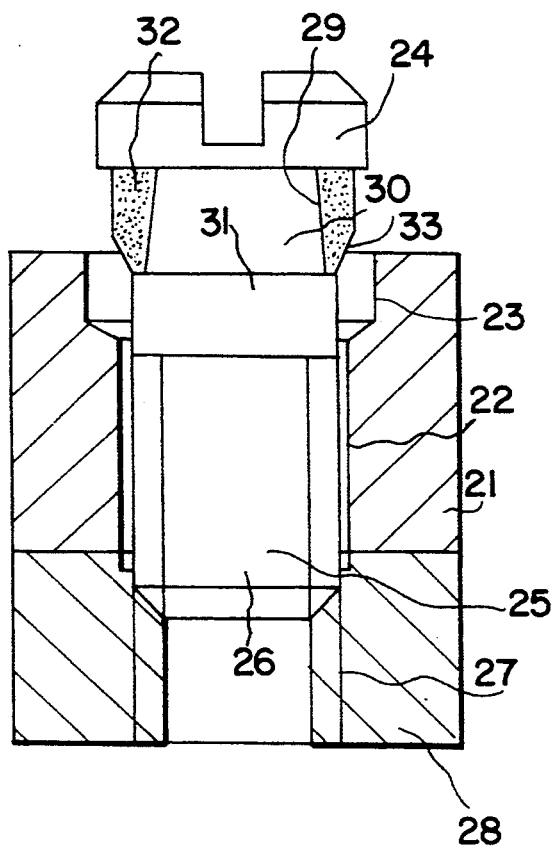
FIG. 3 is a side view of a second embodiment of the present invention.
Figure 4:
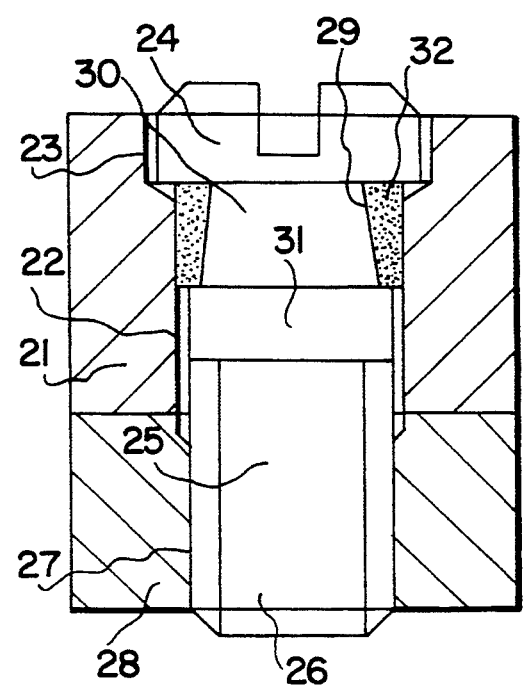
FIG. 4 is also a side view of the second embodiment of the present invention.

In the embodiment shown in FIGS. 3 and 4, the metal rim of the eyeglass frame comprises a first closing lug 21 formed with an unthreaded through bore 22 and at the top of the bore 22 has a recess 23 for receiving the head 24 of the locking screw 25, which has a screw-thread shank end portion 26 that is screwed in a tapped bore 27 of the second closing lug 228 so that the two closing lugs 21 and 28 are connected. In that embodiment, an unintended separation of the joint is prevented in that the screw 12 is formed under the head 24 with a neck, which defines an annular recess 30 and tapers at 29 toward the head 24 and is adjoined at the bottom by an unthreaded top portion 31 of the shank. The neck is surrounded in the recess 30 by a plastic ring 32, which may be injection-molded in place and which has also a downwardly tapered bottom portion 33. The diameters $D_2$ and $D_1$ have again the ratio prescribed hereinbefore so that there is an interference A. Because the plastic ring 12 is conical in its entirety, the locking action will be stronger than in the first embodiment.

Figure 5:
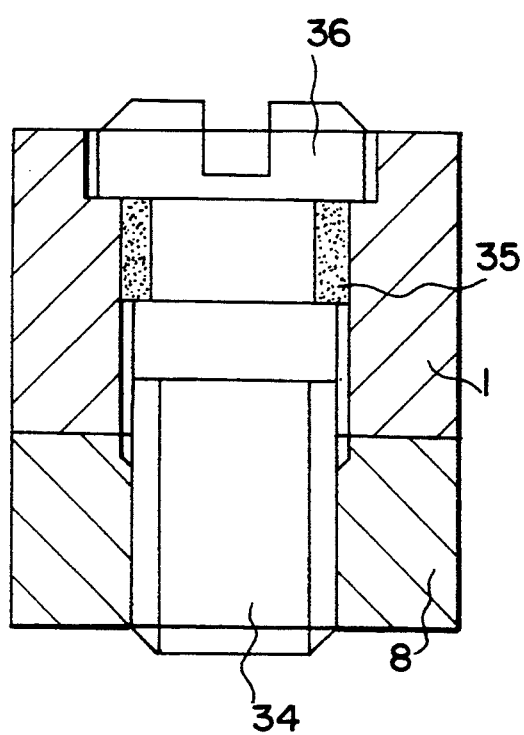
FIG. 5 is a side view of a further embodiment of the present invention.
Figure 6:
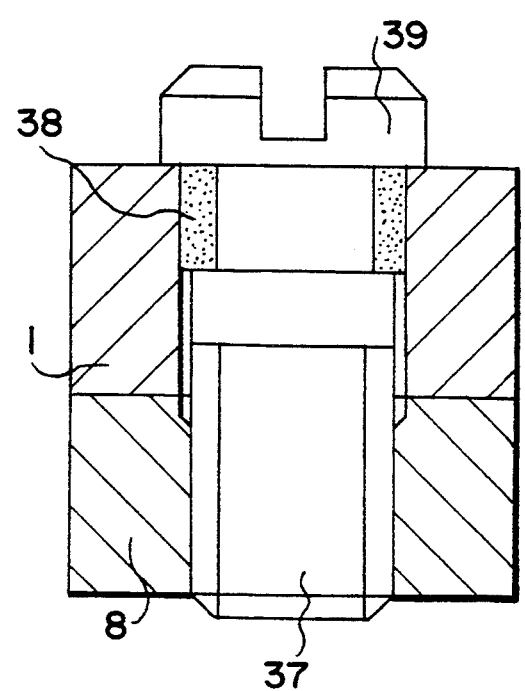
FIG. 6 is a side view of a further embodiment of the present invention.

In FIGS. 5 and 6, two joints between closing lugs 1 and 8, are compared. In FIG. 5, the closing lugs 1 and 8 are connected by a locking screw 34, which has a countersunk head 36 and is provided with a plastic ring 35. In FIG. 6, the closing lugs are connected by a locking screw 37, which is provided with a plastic ring 38 and has a head 39, which rises from the unrecessed closing lug 1.

Figure 7:
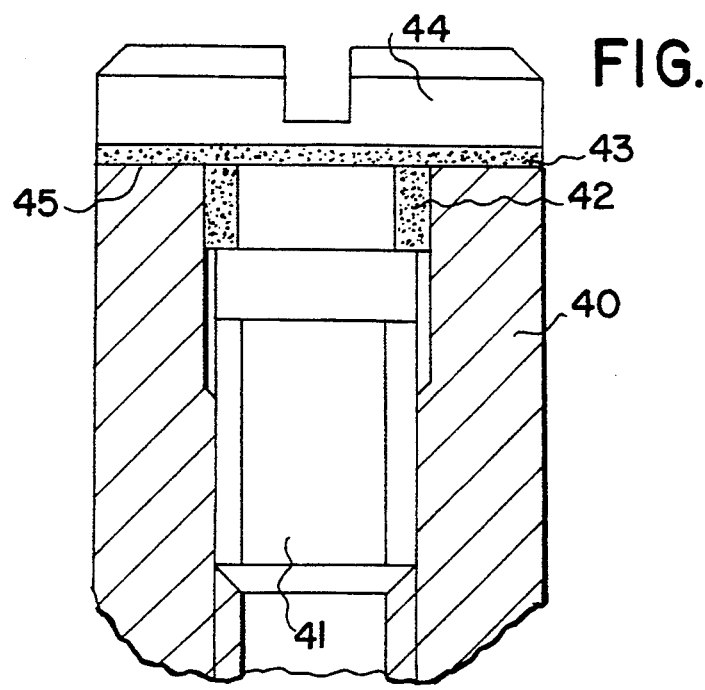
FIG. 7 is a side view of a further embodiment of the present invention.

In the embodiment shown in FIG. 7, the locking screw 41 is screwed into a part 40. The part 40 may be an implant post. The screw 41 has a first plastic ring 42, which surrounds the neck and may be injection-molded, and a second plastic ring 43 arranged on the undersurface of the screw head 44. The first and the second plastic rings 42 and 43 may be injection-molded in place as one part. Because the friction between the second plastic ring 43 and the bearing face 45 is high, the locking action will be stronger than in the embodiments described hereinbefore. The second plastic ring 43 is also a sealing ring.

The screw may also be used for connecting an implant portion 46 with an abutment 47 for supporting an artificial tooth supporting the implant portion. FIGS. 9a and 9b show an implant portion comprising an implant body, which is adapted to be disposed into an opening in a bone of a patient in the vicinity of the occlusal plane and an upper section, which is adapted to be directed away from a base portion of the opening in the bone, when installed.

The upper portion includes a threaded recess. The abutment has a bore, which is open to the said threaded recess. The abutment is connected by a locking screw.

It should be noted that during the tissue healing period, which may vary between some weeks and some months, depending upon the circumstances of each specific case, the threaded recess of the implant body is covered by weak tissue. In this case, the threaded recess must be sealed. The locking screw shown in FIG. 7 may be used as a sealing cap of the threaded recess. After healing is completed, the weak tissue above the screw head 44 will be cut away so that the screw is uncovered. The screw 41 will then be removed.

Figure 8:
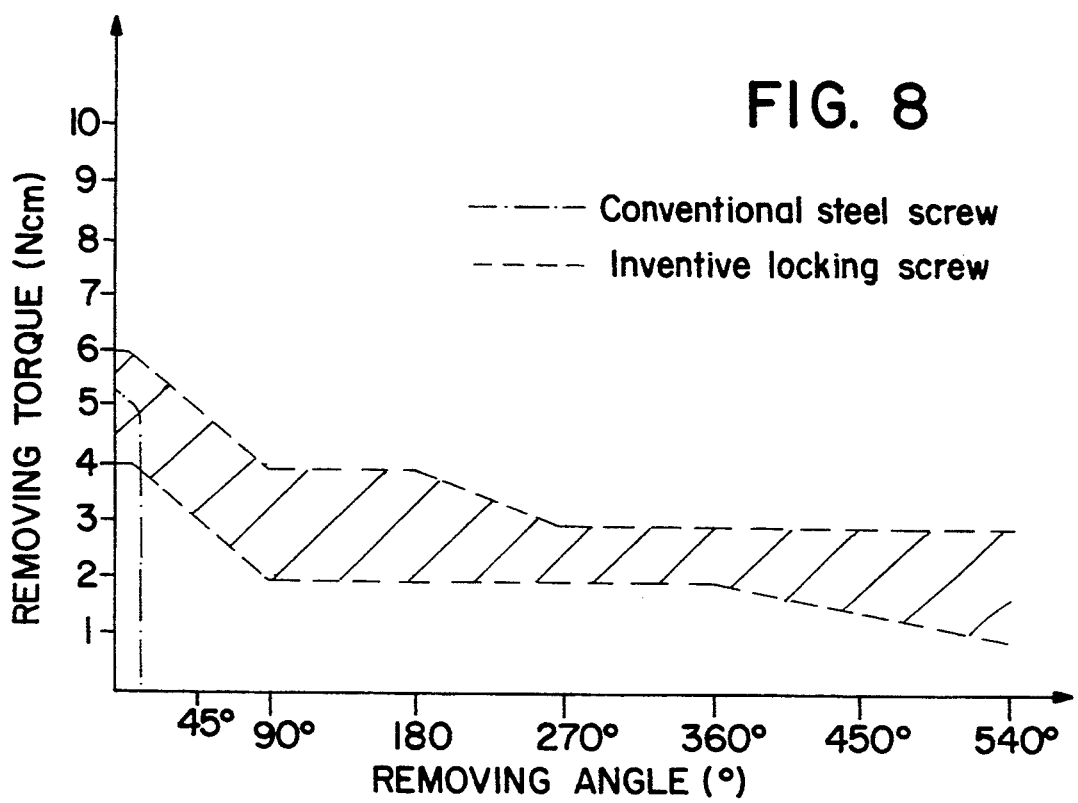
FIG. 8 is a graphical representation of the advantages of the present invention.

The diagram (FIG. 8) shows removing torque about a removing angle. The dash-dot-line shows removing torque about the removing angle of a conventional steel screw. As shown, the removing torque falls rapidly with small values of removing angle.

The area in the diagram shows the removing torque via the removing angle of the inventive locking screw which has been several times screwed and removed. As shown, the locking action is stronger than the locking action of a conventional steel screw.

The inventive locking screw may be used in all cases where a strong locking action is required.

The foregoing is a description of the invention and of the manner and process of making and using the same in such full, clear, concise and exact terms as to enable any person skilled in the art to make and use the same. Those skilled in the art will appreciate and recognize the existence of equivalents to the present invention, and, therefore, the scope of the invention is to be limited only by the appended claims.

What is claimed is:

1. In a locking screw for connecting first and second closing lugs, wherein the first closing lug has an unthreaded through bore and the second closing lug has a tapped bore open to the unthreaded bore, the locking screw has a head to bear on the first closing lug, a screw-threaded shank to be screwed into the tapped bore, and a neck disposed between and recessed from the head and the shank, the improvement comprising:

the neck surrounded by a plastic ring, which protrudes from the shank and frictionally engages the unthreaded through bore; and the shank having an unthreaded portion adjoining the plastic ring.

2. The improvement of claim 1, wherein the plastic ring has been injection-molded in place.

3. The improvement of claim 1, wherein the neck tapers toward the head.

4. The improvement of claim 1, wherein the neck tapers toward the head at an angle of less than 6 degrees.

5. The improvement of claim 1, wherein the plastic ring has adjacent in the shank a portion which tapers toward the shank.

6. The improvement of claim 1, wherein the neck has a knurled surface in contact with the plastic ring.

7. The improvement of claim 1, wherein the plastic ring consists of an amorphous thermoplastic polyether imide.

8. In a metal rim for an eyeglass frame, which rim is formed with first and second closing lugs, wherein the first closing lug has an unthreaded through bore and the second closing lug has a tapped bore open to the unthreaded bore and provided with a locking screw connected to the first and second closing lugs and has a head, which bears on the closing lug, a screw-threaded shank screwed in the tapped bore, and a neck disposed between and recessed from the head and the shank, the improvement comprising:

the neck being surrounded by a plastic ring, which protrudes from the shank and frictionally engages the unthreaded screw bore; and the shank having an unthreaded portion adjoining the plastic ring.

9. The improvement of claim 8, wherein the ratio of the outside diameter of the plastic ring to the diameter of the unthreaded through bore is 1.05 to 1.09.

10. The improvement of claim 8, wherein the first closing lug is formed with a recess, which opens into the unthreaded through bore and contains the head.

11. A locking screw, which has a head adapted to bear on a part having a bore with an unthreaded portion and tapped portion, a screw-threaded shank adapted to be screwed into the tapped bore, and a neck disposed between and recessed from the head and the shank, the improvement comprising:

the neck being surrounded by a plastic ring, which protrudes from the shank and is adapted to frictionally engage the unthreaded through bore; and the shank having an unthreaded portion adjoining the plastic ring.

12. Locking screw of claim 11, wherein the shank has an unthreaded portion adjoining the plastic ring.

13. Locking screw of claim 11, wherein the plastic ring has been injection-molded in place.

14. Locking screw of claim 11, wherein the neck tapers toward the head.

15. Locking screw of claim 11, wherein the ratio of the outside diameter of the plastic ring to the diameter of the unthreaded through bore is 1.05 to 1.09.

16. Locking screw of claim 11, wherein the plastic ring consists of an amorphous thermoplastic polyether imide.

17. Locking screw of claim 11, wherein a second plastic ring is arranged on the undersurface of the screw head.

18. Locking screw of claim 17 characterized in that the screw is used as a sealing cup.

19. In an implant portion of an oral implant designed for supporting an artificial tooth structure comprising an implant body disposed in an opening in a bore of a patient in the vicinity of the occlusal plane and an upper section directed away from a base portion of the opening in the bone, when installed, including a threaded recess for connecting an abutment for supporting an artificial tooth structure to the implant portion, the improvement comprising:

the abutment having a bore open to the threaded recess;

a locking screw having a head bearing on the abutment;

a screw-threaded shank screwed into the threaded recess; and a neck disposed between and recessed from the head and the shank, the neck being surrounded by a plastic ring, which protrudes from the shank and frictionally engages an unthreaded through bore, and the shank having an unthreaded portion adjoining said plastic ring.

20. The improvement of claim 19, wherein the abutment is formed with a recess, which opens into the unthreaded through bore and contains the bore.

* * * * *